United States Patent
Andreoli et al.

(10) Patent No.: US 10,399,793 B2
(45) Date of Patent: Sep. 3, 2019

(54) METHOD AND SYSTEM FOR CONTROLLING THE COEFFICIENT OF FRICTION BETWEEN A CONVEYOR SURFACE AND THE TRANSPORTED PRODUCTS

(71) Applicant: REXNORD FLATTOP EUROPE B.V., s-Gravenzande (NL)

(72) Inventors: Andrea Andreoli, Modena (IT); Cornelis Hendrik Mijndert Menke, 's-Gravenzande (NL); Justin Michael Stefanko, Waukesha, WI (US)

(73) Assignee: REXNORD FLATTOP EUROPE B.V., 'S-Gravenzande (NL)

( * ) Notice: Subject to any disclaimer, the term of this patent is extended or adjusted under 35 U.S.C. 154(b) by 0 days.

(21) Appl. No.: 16/080,806

(22) PCT Filed: Mar. 1, 2017

(86) PCT No.: PCT/NL2017/050127
§ 371 (c)(1),
(2) Date: Aug. 29, 2018

(87) PCT Pub. No.: WO2017/150976
PCT Pub. Date: Sep. 8, 2017

(65) Prior Publication Data
US 2019/0084772 A1    Mar. 21, 2019

(30) Foreign Application Priority Data
Mar. 1, 2016    (NL) .................................... 2016340

(51) Int. Cl.
*B65G 45/02* (2006.01)
*B65G 43/04* (2006.01)
(Continued)

(52) U.S. Cl.
CPC ............. *B65G 45/02* (2013.01); *B65G 43/04* (2013.01); *B65G 45/18* (2013.01); *G01N 19/02* (2013.01)

(58) Field of Classification Search
CPC ........ B65G 45/02; B65G 43/00; B65G 43/04; B65G 45/18; G01N 19/02
(Continued)

(56) References Cited

U.S. PATENT DOCUMENTS 4,915,209 A * 4/1990 Canziani ................ B65G 43/08
                                                198/502.2
4,930,600 A * 6/1990 Kumar ...................... B61K 3/02
                                                198/500

(Continued)

FOREIGN PATENT DOCUMENTS

DE          43 37 037 A1     5/1995
DE     10 2014 105894 A1    10/2015
(Continued)

OTHER PUBLICATIONS

International Search Report and Written Opinion dated Jun. 13, 2017 in connection with PCT/NL2017/050127.

*Primary Examiner* — James R Bidwell
(74) *Attorney, Agent, or Firm* — Quarles & Brady LLP

(57) ABSTRACT

Method and system (10) for transporting products (2). A conveyor surface (1) is moving at a conveyor velocity (VI). Products (2) are provided on the conveyor surface (1) in a measurement zone (M). The products (2) move through the measurement zone (M) with a product velocity (V2) that is at least initially different than the conveyor velocity (VI). A contact between the products (2) and the relatively moving conveyor surface (1) causes the products (2) to accelerate or decelerate (a) in the measurement zone (M) depending on a kinetic friction coefficient ($\mu_k$) there between. A control signal (S) is indicative of the acceleration or deceleration (a)

(Continued)

of the products (2) in the measurement zone (M). The kinetic friction coefficient (μk) is controlled based on the control signal (S) to keep the acceleration or deceleration (a) within a predetermined threshold range.

14 Claims, 11 Drawing Sheets

(51) Int. Cl.
*G01N 19/02* (2006.01)
*B65G 45/18* (2006.01)

(58) Field of Classification Search
USPC .............................................. 198/500, 502.1
See application file for complete search history.

(56) References Cited

U.S. PATENT DOCUMENTS

| | | | |
|---|---|---|---|
| 8,343,898 B2* | 1/2013 | Ruhr | C10M 173/025 |
| | | | 198/500 |
| 2007/0119686 A1* | 5/2007 | Divisi | B65G 45/02 |
| | | | 198/502.1 |
| 2016/0041086 A1* | 2/2016 | Jacques | G01N 19/02 |
| | | | 184/6.1 |

FOREIGN PATENT DOCUMENTS

| | | | | |
|---|---|---|---|---|
| EP | 1790968 | * | 5/2007 | ............ B65G 45/02 |
| JP | H10 221239 A | | 8/1998 | |

* cited by examiner

METHOD AND SYSTEM FOR CONTROLLING THE COEFFICIENT OF FRICTION BETWEEN A CONVEYOR SURFACE AND THE TRANSPORTED PRODUCTS

CROSS-REFERENCE TO RELATED APPLICATIONS

This application represents the national stage entry of PCT International Application No. PCT/NL2017/050127 filed on Mar. 1, 2017 and claims priority to Netherlands Patent Application No. 2016340 filed on Mar. 1, 2016, the contents of which are hereby incorporated by reference as if set forth in their entirety herein.

TECHNICAL FIELD AND BACKGROUND

The present disclosure relates to a method and system for transporting products on a conveyor surface, in particular measurement and control of friction between the products and the conveyor surface.

For example, US 2007/0119686 A1 describes a conveyor that comprises a conveyor belt with which a lubricant dispensing device is associated. It also comprises a device for measuring a quantity proportional to the friction coefficient between the conveyor belt and the bottles and connected to control means for controlling said lubricant dispensing device in such a manner as to regulate the lubricant amount in order to maintain the measured quantity within a predetermined range. The lubrication regulating process for a conveyor belt of a conveyor for bottles or containers in general consists of measuring a quantity indicative of the friction coefficient between the conveyor belt and bottles and controlling the lubricant feed onto the conveyor belt such as to maintain this quantity within a predetermined range. According to the prior art, the friction coefficient is measured using a measuring device that comprises a slider connected via elastic means to a sensor able to measure the force acting on it and provided with a contact portion slidably associated with said conveyor belt, such that during operation said slider is dragged by said conveyor belt and is retained by said elastic means which, by exerting a force on the sensor, enable a signal to be measured is indicative of the friction coefficient between the conveyor belt and the contact portion, which is proportional to the friction coefficient between the conveyor belt and the bottles.

Unfortunately, the known system relies on a sensor which can take valuable space on the conveyor belt and may require substantial adaptation of the conveyor system. Furthermore, the known sensor only detects friction at the contact position which may be not accurately reflect all parts of the conveyor belt, e.g. at adjacent positions. There is yet a need for an improved conveyor system which alleviates these or other problems.

SUMMARY

A first aspect of the present disclosure provides a method of transporting products. A conveyor surface is provided moving at a certain conveyor velocity. Products are provided on the conveyor surface in a measurement zone. The products move through the measurement zone with a product velocity that is at least initially different than the conveyor velocity. A contact between the products and the relatively moving conveyor surface causes the products to accelerate or decelerate in the measurement zone. The accelerate or decelerate may depend on a kinetic friction coefficient there between. A control signal is derived from the acceleration or deceleration of the products in the measurement zone. The kinetic friction coefficient is controlled based on the control signal to keep the acceleration or deceleration within a predetermined threshold range.

The inventors find that the acceleration or deceleration of products on a relatively moving conveyor surface can provide a good indicator of the kinetic friction coefficient. Without being bound by theory, it is noted that the kinetic friction coefficient may be proportional to the acceleration or deceleration of the products while they are sliding over the conveyor surface at a product velocity that is different from the conveyor velocity. By deriving the control signal from the acceleration or deceleration of the products themselves, an additional contact sensor is not required. Accordingly, the conveyor system needs minimal or no adaptation because the products themselves are used as sensor elements. Since the products may typically slide over the whole conveyor surface, the friction coefficient at multiple positions may be determined. By keeping the acceleration or deceleration within a predetermined threshold range, it can be prevented e.g. that products such as bottles topple over when they experience sudden acceleration. Also damage to products such as packages can be prevented.

By basing the control signal on a sensor signal indicative of a time-dependent position of one or more of the products, the acceleration can be derived. By using an optical measurement of an acceleration of one or more of the products, it is not necessary to provide any contact sensor. For example, a simple camera can be used to record images of the moving products from which images the position and acceleration of the products can be derived. For example, an existing camera system may be adapted with image recognition software to determine a time dependent position of the products. For example, one or more of the products may be tagged in software or using an otherwise detectable tag to allow tracking a position of the one or more tagged products.

By changing a surface property of the conveyor surface and/or surface of the products, the kinetic friction coefficient may be controlled. For example, the kinetic friction coefficient may be controlled by applying a controlled amount of lubricant to the conveyor surface and/or the products. For example, the applied amount of lubricant may be increased when the acceleration or deceleration is outside the predetermined threshold range, e.g. when the acceleration is too high. Alternatively, or in addition, the kinetic friction coefficient may be controlled by controlling a degree of cleaning of the conveyor surface, e.g. by applying a cleaning solution and/or activating a cleaning brush when the acceleration is too high.

Optionally, the kinetic friction coefficient may be calculated based on an acceleration or deceleration of one or more of the products. For example, the acceleration or deceleration can be calculated based on a measurement of a time-dependent position of one or more of the products. Alternatively, or in addition, any other quantity which may be proportional to the kinetic friction coefficient and/or acceleration/deceleration of the products may be calculated. The control signal may be calculated locally or off-site. For example camera images may be sent to a remote location where a control signal is calculated based on the images. The control signal may be received by a friction adjustment device to adjust the friction of the conveyor surface and/or the products. Some aspects of the present methods may be embodied in a computer readable medium with software instruction that when read by a computer causes the computer to execute the method as described herein.

Further aspects of the present disclosure provide a conveyor system for transporting products. A conveyor surface is configured to move at a certain conveyor velocity. The products are guided onto the conveyor surface to move through a measurement zone with a product velocity that is at least initially different than the conveyor velocity. A contact between the products and the relatively moving conveyor surface causes the products to accelerate or decelerate in the measurement zone depending on a kinetic friction coefficient there between. A sensor is configured to measure the acceleration or deceleration of the products in the measurement zone for calculating a control signal indicative of the acceleration or deceleration. A friction adjustment device is configured to control the kinetic friction coefficient based on the control signal to keep the acceleration or deceleration within a predetermined threshold range.

By providing an optical sensor a time-dependent position of the products can be easily measured in an existing conveyor system with minimal adaptation. For example, a camera may be configured to record images of the measurement zone at different times, e.g. every 0.1 seconds. An image processor may process the recorded images and calculate a time-dependent position of one or more of the products based on the recorded images. By programming the image processor with image recognition software e.g. a visual marker associated with (part of) a product may be tracked. For example, a bottle cap or other visual marker may be tracked between different images to determine a displacement of the product. Using the time dependent position, e.g. an acceleration calculator may calculate an acceleration or deceleration of one or more of the products based on the time-dependent position of the one or more of the products. A friction controller may compare the acceleration or deceleration of one or more of the products to the predetermined threshold range and to adjust the control signal based on the comparison. Of course these and other devices as described herein may be implemented in hardware and/or software. One or more devices may be integrated or divided into further sub-units. The friction adjustment device may e.g. comprise a dispenser configured to apply a variable amount of lubricant and/or cleaning solution to the conveyor surface and/or the products.

BRIEF DESCRIPTION OF DRAWINGS

These and other features, aspects, and advantages of the apparatus, systems and methods of the present disclosure will become better understood from the following description, appended claims, and accompanying drawing wherein:

DESCRIPTION OF EMBODIMENTS

Figure 1A:
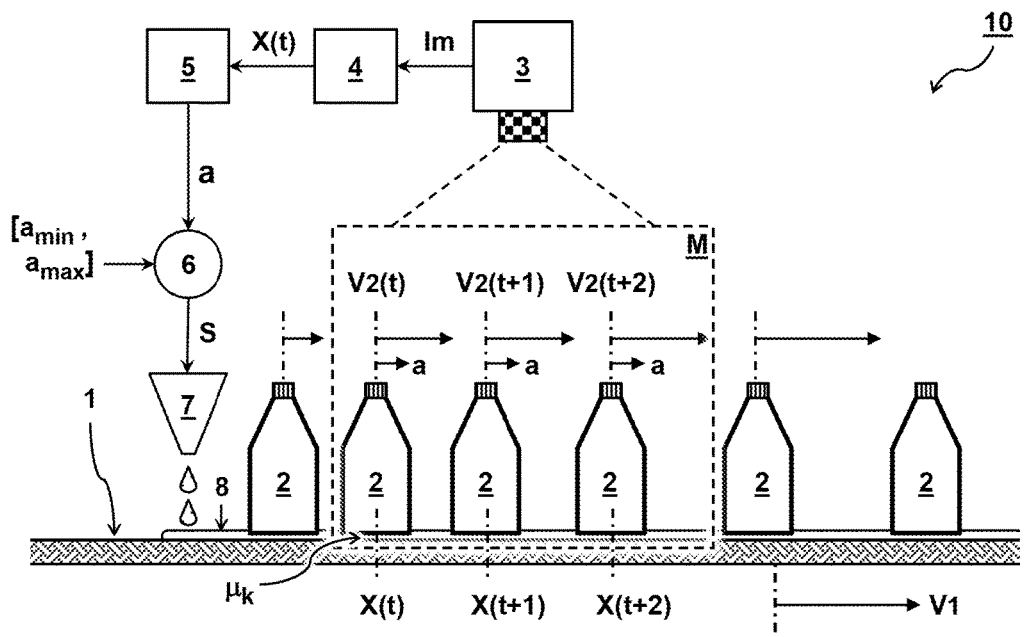
FIG. 1A schematically illustrates an embodiment of a system for transporting products on a conveyor surface.

In some instances, detailed descriptions of well-known devices and methods may be omitted so as not to obscure the description of the present systems and methods. Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise it will be understood that when a connection between structures or components is described, this connection may be established directly or through intermediate structures or components unless specified otherwise.

The invention is described more fully hereinafter with reference to the accompanying drawings, in which embodiments of the invention are shown. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

FIG. 1A schematically illustrates an embodiment of a conveyor system 10. The figure shows a product 2 being at different positions $X(t)$, $X(t+1)$, $X(t+2)$ for different times t, t+1, t+2. The time-dependent position $X(t)$ may be used to calculate a time dependent velocity $V_2(t)$, $V_2(t+1)$, $V_2(t+2)$ of the products 2 and/or an acceleration "a" of the products, e.g. taking the double derivative of the position "X" over time "t". For example, the products 2 are bottles, cans, or other products. For example, the products 2 are boxes (not shown).

In one embodiment, the system 10 comprises a conveyor surface 1 configured to move at a conveyor velocity V1. The products 2 are provided onto the conveyor surface 1 to move through the measurement zone M with a product velocity V2 that is at least initially different than the conveyor velocity V1. A contact between the products 2 and the relatively moving conveyor surface 1 causes the products 2 to accelerate or decelerate "a" in the measurement zone M depending on a kinetic friction coefficient "μk" there between.

In one embodiment, the system 10 comprises a sensor 3 configured to measure the acceleration or deceleration "a" of the products 2 in the measurement zone M. Accordingly a control signal "S" may be calculated indicative of the acceleration or deceleration "a". Preferably, the sensor 3 comprises an optical sensor configured to optically measure a time-dependent position X(t) of the products. For example, the sensor 3 comprises a camera configured to record images Im of the measurement zone M at different times t, e.g. every 0.1 seconds. Also other intervals may be used.

In another or further embodiment, the system comprises an image processor 4 configured to process the recorded images Im and calculate a time-dependent position X(t) of one or more of the products 2 based on the recorded images Im. In another or further embodiment, the image processor 4 is programmed with image recognition software to recognize a visual marker associated with part of a product, e.g. bottle cap, and track a position of the visual marker between different images.

In one embodiment, the system 10 comprises an acceleration calculator 5 configured to calculate an acceleration or deceleration "a" of one or more of the products 2 based on the time-dependent position X(t) of the one or more of the products 2. In one embodiment, the system 10 comprises a friction controller 6 configured to compare the acceleration or deceleration "a" of one or more of the products 2 to a predetermined threshold range [$a_{min}, a_{max}$] and to adjust the control signal "S" based on the comparison. In another or further embodiment, the system 10 comprises a friction adjustment device 7 configured to control the kinetic friction coefficient "μk" based on the control signal "S" to keep the acceleration or deceleration "a" within a predetermined threshold range [$a_{min}, a_{max}$]. For example, the threshold range is set to prevent toppling of the products, e.g. bottles or cans, and/or to prevent damage to the products, e.g. boxes or other containers.

In one embodiment, the friction adjustment device 7 comprises a lubricant dispenser configured to apply a variable amount of lubricant 8 to the conveyor surface 1 and/or the products 2. Alternatively, or in addition, the friction adjustment device 7 comprises a cleaning device, e.g. controllable brush to reduce friction by cleaning the conveyor surface 1. Alternatively, or in addition, a cleaning fluid may be applied to the conveyor surface and/or bottles. It will be appreciated that cleaning the conveyor surface may affect the current and/or future friction in some cases. For example, timely cleaning of a spilled beverage may prevent friction increase when the beverage would otherwise dry up e.g. leaving a sugary residue.

In some embodiments, a separate lubricant and cleaning solution is used. For example an oil-based lubricant and/or a soap-based cleaning solution. Using specialized substances depending on the circumstances (insufficient friction and/or spillage) may be more effective and prevent waste. In some embodiments, the same substance can be used for both lubricating and cleaning. For example, a soap solution may act as a lubricant and/or as a cleaning solution. Also a mix of substances can be used. By using a substance with combined effect, the apparatus can be more simple. Also other friction reducing and/or cleaning substances may be used.

The figures illustrate various methods of transporting products using one or more conveyor surfaces. According to some aspects, a conveyor surface 1 is provided moving at a conveyor velocity V1. Products 2 are provided on the conveyor surface 1 in a measurement zone M. The products 2 move through the measurement zone M with a product velocity V2 that is at least initially different than the conveyor velocity V1. A contact between the products 2 and the relatively moving conveyor surface 1 causes the products 2 to accelerate or decelerate a in the measurement zone M depending on a (kinetic) friction there between. The friction may be controlled to keep the acceleration or deceleration "a" within a predetermined threshold range.

In one embodiment, the control signal "S" is based on a sensor signal Si indicative of a time-dependent position X(t) of one or more of the products 2 in the measurement zone M. For example, the control signal "S" is based on an optical measurement of an acceleration of one or more of the products 2 in the measurement zone M. In another or further embodiment, the method comprises recording a sequence of images of the measurement zone M where the products 2 are accelerating or decelerating as a result of the contacting relatively moving conveyor surface 1. In another or further embodiment, a time-dependent position X(t) of at least one of the products 2 is determined based on the recorded images. In another or further embodiment, the control signal "S" is based on an the time-dependent position X(t) of the at least one of the products 2. Some embodiments may comprise calculating the kinetic friction coefficient "μk" based on an acceleration or deceleration "a" of one or more of the products 2. Another or further embodiment comprises, tagging one or more of the products 2 and tracking a position X of the one or more tagged products 2. Products may be tagged e.g. by appropriate masking of captured image frames or otherwise.

In one embodiment, the kinetic friction coefficient "μk" is controlled by changing a surface property of the conveyor surface 1 and/or surface of the products 2. For example, the kinetic friction coefficient "μk" is controlled by applying a controlled amount of lubricant 6 to the conveyor surface 1 and/or the products 2. For example, the applied amount of lubricant 6 is increased when the acceleration or deceleration "a" is outside the predetermined threshold range, e.g. when the acceleration is too high. In another or further embodiment, the kinetic friction coefficient "μk" is controlled by controlling a degree of cleaning of the conveyor surface 1, e.g. by applying a cleaning solution and/or activating a cleaning brush when the acceleration is too high.

In one embodiment, the acceleration or deceleration "a" is calculated based on a measurement of a time-dependent position X(t) of one or more of the products 2. Alternatively, or in addition, a time- or position dependent velocity may be used to infer the preceding acceleration or deceleration of products. Calculation and processing may be done in hardware and/or software. Some hardware may be at a remote location, e.g. connected via a network. Some hardware may be local, e.g. a camera to capture images of the products. In one embodiment, the system comprises hardware and/or software linking the sensor 3 with the friction regulating device 7 to carry out the intended use.

One aspect of the present disclosure provides a non-transient computer readable medium with software instruction that when read by a computer causes the computer to execute the method as described herein. In one embodiment, a non-transient computer readable medium has software instruction that causes a computer to execute a method comprising receiving a measurement of products 2 moving through a measurement zone M on a conveyor surface 1 as described herein. For example, the measurement may be an optical measurement, e.g. camera images of the products. Based on the measurement, a control signal S may be calculated that is indicative of an acceleration or deceleration "a" of the products 2. In some embodiments, the control signal S may be sent out or processed internally for controlling the kinetic friction coefficient µk based on the control signal S. In this way the acceleration or deceleration may be kept within a predetermined threshold range.

Without being bound by theory, some aspects and advantages of the present disclosure may be based on the following insights explained with reference to FIG. 1B which schematically illustrates an analysis of friction forces "$F_k$" between a product 2 and a conveyor surface 1.

Kinetic (or dynamic) friction occurs when two objects are moving relative to each other and rub together (like a sled on the ground). The coefficient of kinetic friction is typically denoted as µk, and is usually less than the coefficient of static friction for the same materials.

Figure 1B:
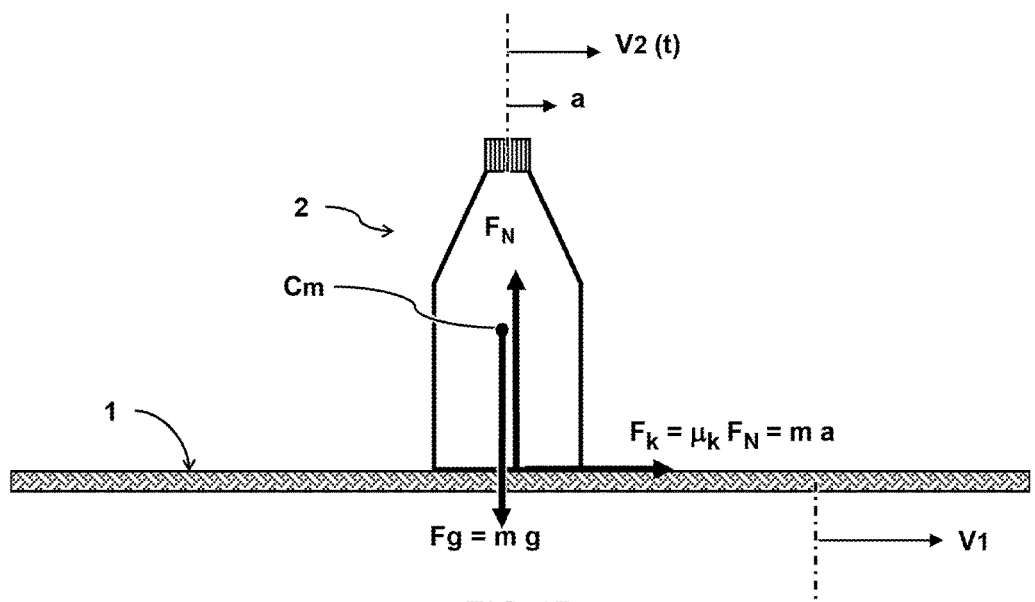
FIG. 1B schematically illustrates an analysis of friction forces between a product and a conveyor surface.

As illustrated in the FIG. 1B, the gravitational force "$F_g$" acting on the centre of mass "$C_m$" of the product having mass "m" equals $$F_g = m \cdot g, \quad (1)$$

where "g" is a constant on earth equal to about 9.8 m/s². When standing on the conveyor surface, the product experiences an equal and opposite normal force "$F_N$" from the conveyor surface:

$$F_N = F_g. \quad (2)$$

When there is relative movement between the product and the conveyor surface (V2≠V1), a kinetic friction force "$F_k$" may act between the product and the conveyor surface which is proportional to the kinetic friction coefficient "µk" and the normal force "$F_N$":

$$F_k = \mu_k \cdot F_N \quad (3)$$

The friction force "$F_k$" causes an acceleration "a" while V2<V1, or deceleration while V2>V1, according to the relation $$F_k = m \cdot a \quad (4)$$

By combining the above equations it can be shown that the acceleration "a" of the product on the conveyor surface is proportional to the kinetic friction coefficient "µk":

$$\mu_k \cdot F_N = m \cdot a \quad (5)$$

$$\mu_k \cdot m \cdot g = m \cdot a \quad (6)$$

$$\mu_k \cdot g = a \quad (7)$$

It will be appreciated that the kinetic friction coefficient "µk" may thus be independent of the mass "m" of the product. Preferably, the conveyor surface is horizontal. In that way the gravitational force on the products does not cause acceleration and it may be assumed that all acceleration or deceleration is a result friction forces. Alternatively, on an inclining or declining conveyor surface, the friction forces may also be calculated from the acceleration and/or velocity by taking into account any residual gravitational forces.

Figure 3A:
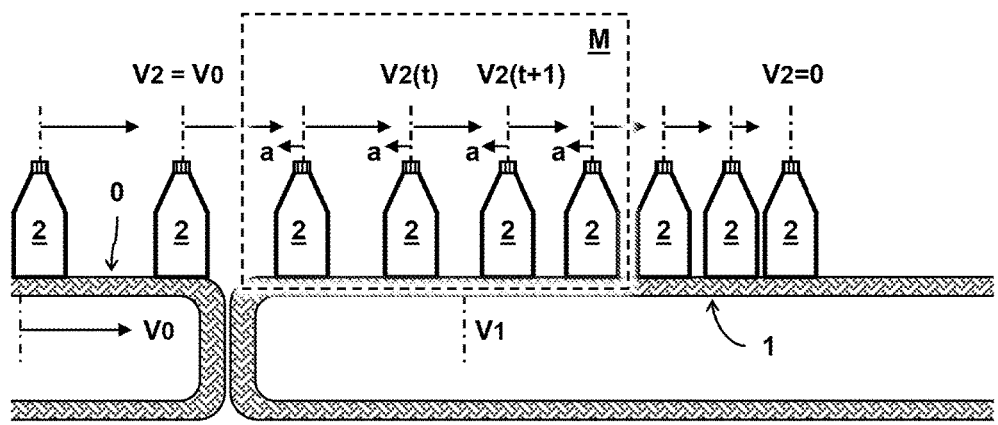
FIG. 3A schematically illustrates an embodiment where products are guided onto a non-moving surface.
Figure 3B:
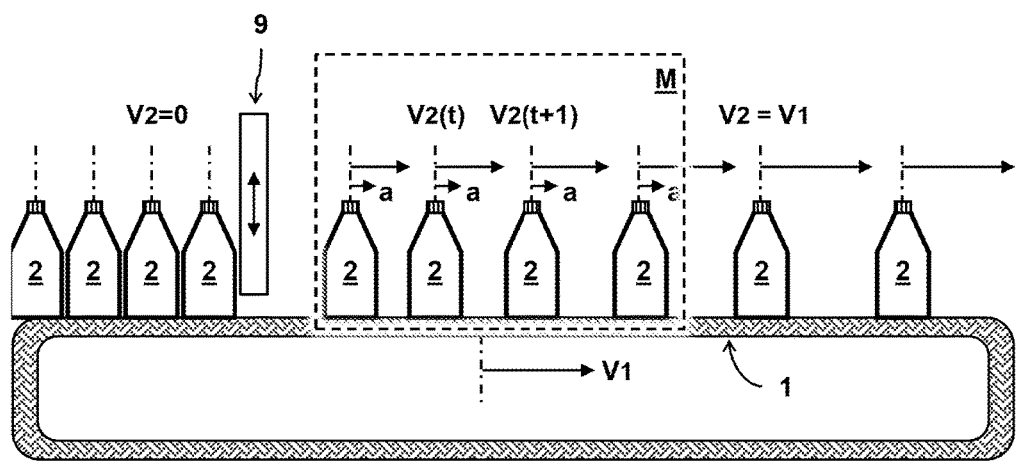
FIG. 3B schematically illustrates an embodiment where products are held and released on a moving conveyor surface.
Figure 4:
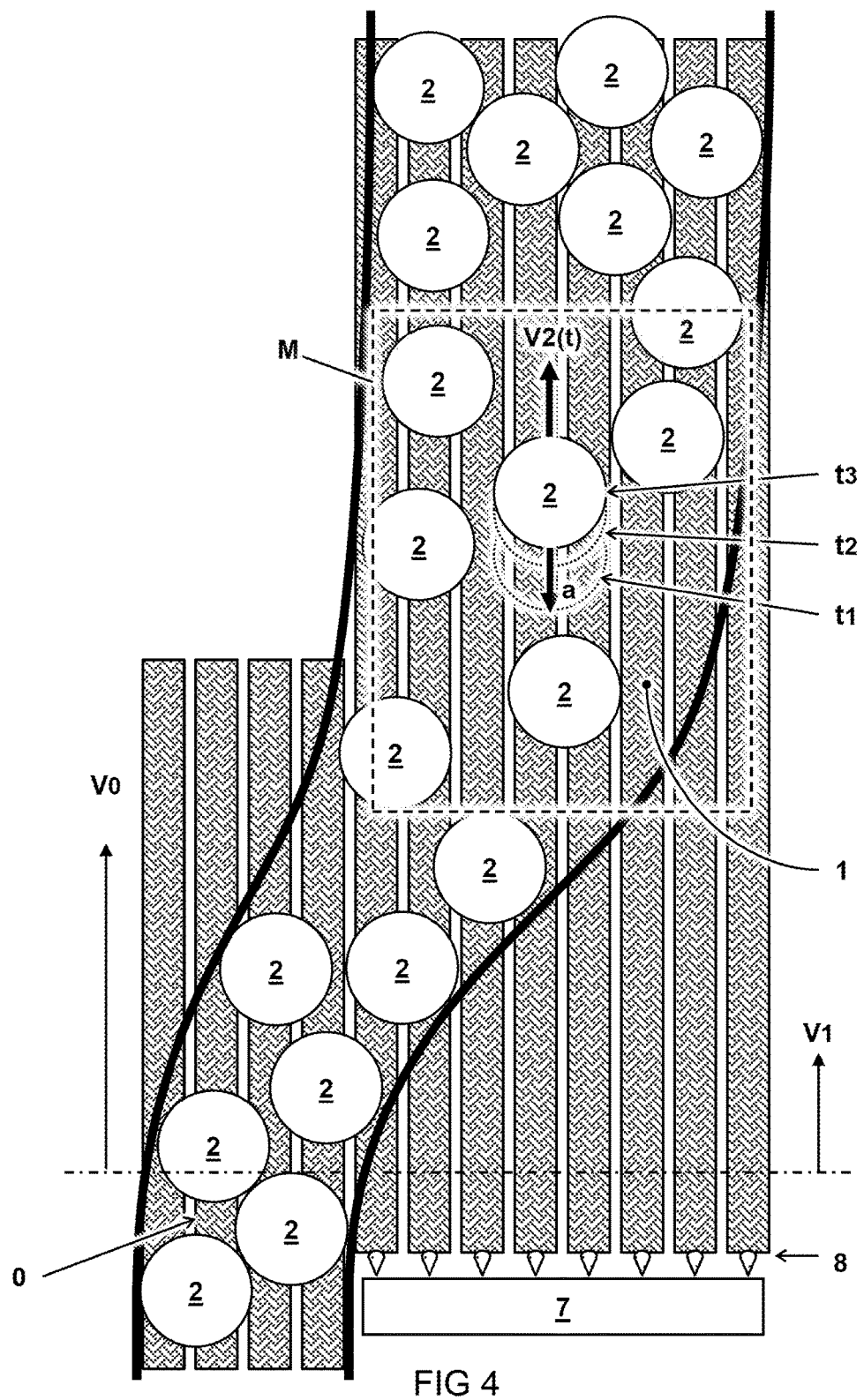
FIG. 4 schematically illustrates a top view of an embodiment where products are moved between adjacent conveyor belts.

FIGS. 2-4 illustrate embodiments, wherein the conveyor surface 1 is a destination conveyor surface 1, the system further comprising an origin conveyor surface 0 configured to lead the products 2 from the origin conveyor surface 0 to the destination conveyor surface 1. A transition from the origin conveyor surface 0 to the destination conveyor surface 1 causes the products 2 to accelerate or decelerate a in the measurement zone M on the destination conveyor surface 1. For example, the origin conveyor surface 0 is configured to move at a different velocity V0 than the destination conveyor surface 1.

Figure 2A:
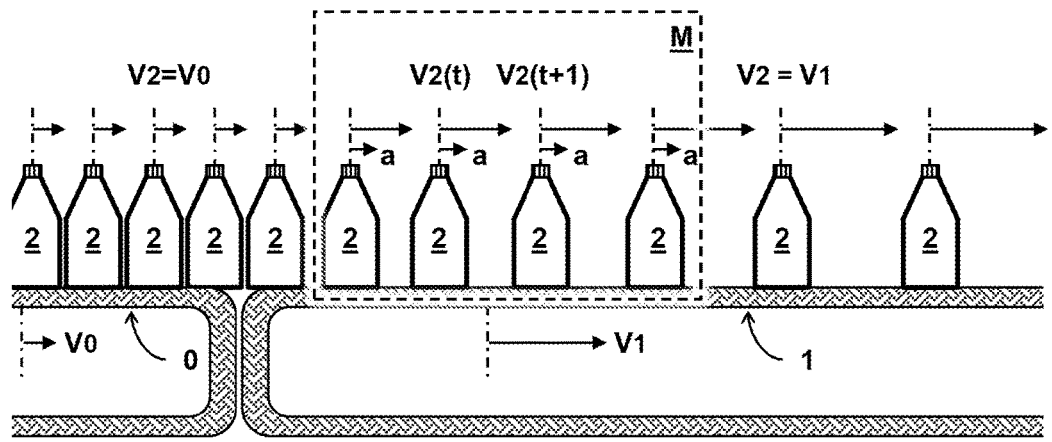
FIG. 2A schematically illustrates an embodiment where products are moved from a slow moving belt to a fast moving belt.

FIG. 2A illustrates an embodiment wherein the origin conveyor surface 0 moves at a lower velocity V0 than that of the destination conveyor surface 1 moving at velocity V1. The difference in velocity causes the products 2 to accelerate (indicated with arrow "a") upon contact with the destination conveyor surface 1. For example, the measurement zone M is at the beginning of the destination conveyor surface 1.

Figure 2B:
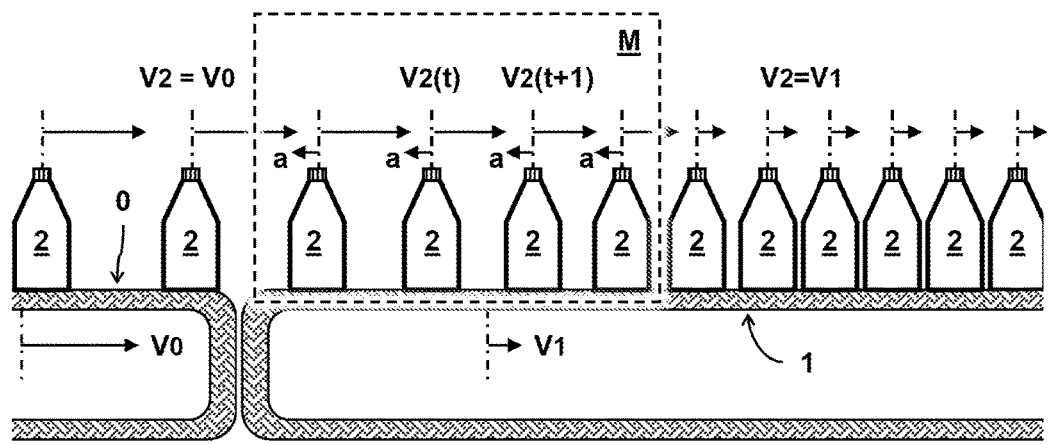
FIG. 2B schematically illustrates an embodiment where products are moved from a fast moving belt to a slow moving belt.

FIG. 2B illustrates an embodiment wherein the origin conveyor surface 0 moves at a higher velocity V0 than that of the destination conveyor surface 1 moving at velocity V1. The difference in velocity causes the products 2 to decelerate (indicated with arrow "a") upon contact with the destination conveyor surface 1.

FIG. 3A schematically illustrates an embodiment wherein the origin conveyor surface 0 moves at a velocity V0 and the destination conveyor surface 1 is at least initially not moving. The difference in velocity causes the products 2 to decelerate upon contact with the destination conveyor surface 1 similar as in FIG. 2B.

FIG. 3B schematically illustrates an embodiment comprising a holding device 9 configured to temporarily hold a position of one or more of the products 2 while they are on the conveyor surface 1. For example a screen or bar may hold the advancement of products while a batch is loaded into a container. In one embodiment, the measurement zone M is behind the holding device 9 to measure acceleration of one or more of the products 2 after being released from the holding device 9.

FIG. 4 schematically illustrates a top view of an embodiment wherein the origin conveyor surface 0 is configured to move parallel and adjacent to the destination conveyor surface 1. For example, the system comprises a rail configured to move the products laterally between the origin conveyor surface 0 and the destination conveyor surface 1. For example the figure illustrates one of the products 2 experiencing a deceleration "a" of its velocity $V_2(2)$ at different times $t_1$, $t_2$, $t_3$.

Figure 5A:
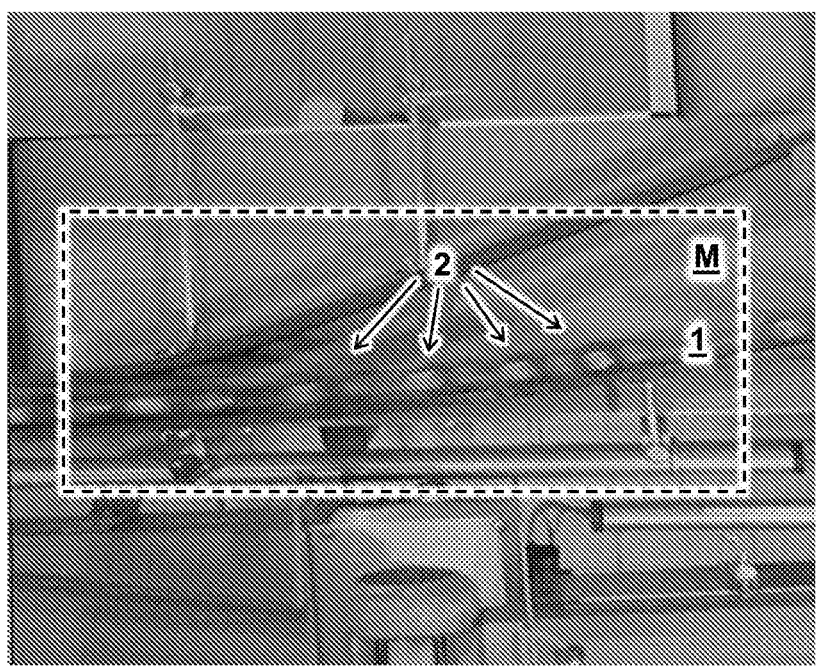
FIGS. 5A and 5B illustrate a captured image frame and corresponding mask pattern of relatively isolated products moving on a conveyor surface according to an embodiment.
Figure 5B:
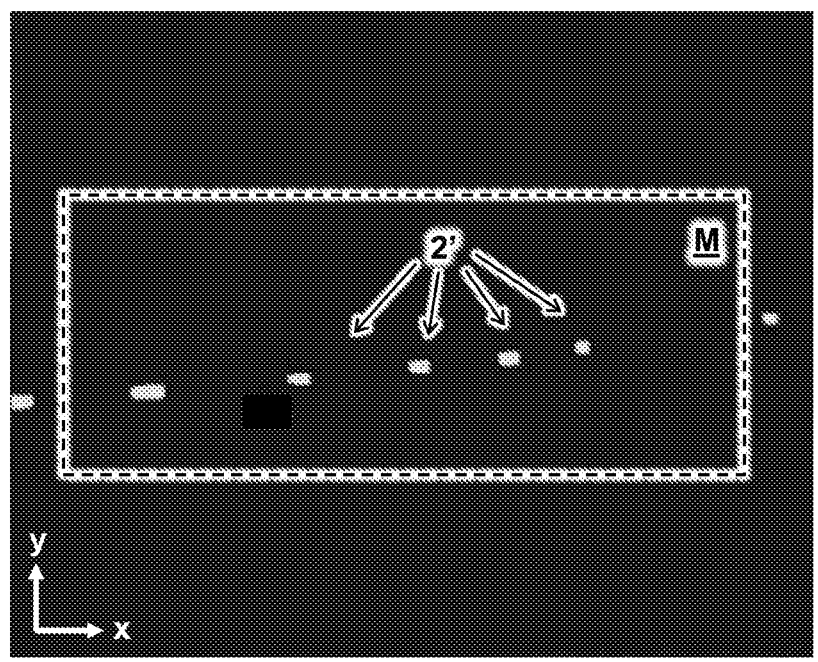

FIGS. 5A and 5B illustrate a captured image frame (originally color) and corresponding mask pattern (black and white) of products 2 moving on a conveyor surface 1 through a measurement zone "M". In the masked image shown, the products are identified by corresponding groups of white pixels 2' on a black background. Of course the shown mask image is only an example representation.

In one embodiment, captured image frames of products on a conveyor surface are masked e.g. by a dedicated or integrated image processor. In some embodiments, masking comprises setting thresholds for pixel values in captured images to isolate distinctive features of the products from the surroundings. For example, in the embodiment shown, the bottle caps have a distinctive color that can be isolated by suitable masking of the captured frame. In some embodiments, environmental features are removed from the masked image by comparing the captured imaged with a reference image without products. To further remove unwanted features (e.g. reflections and shadows), the measurement zone M can be adjusted to narrowly fit around the expected or measured trajectory of the products 2.

In the embodiment shown, the products 2 are relatively isolated from one another. This may allow their individual positions 2' to be identified in the masked image. Depending on a capture frequency or camera shutter time, the position of the products 2 can be more or less specific. For example, the position of a product may a derived from an average position of a group of interconnected (white) pixels. In some embodiments, masked images of products are processed to calculate a control signal for controlling the friction. For example, the masked image may be processed to track a time-dependent position x,y of (groups of) masked pixels through a sequence of different frames and a velocity and/or acceleration can be determined based on the changing position to calculate a control signal for controlling the friction as described herein.

Figure 6A:
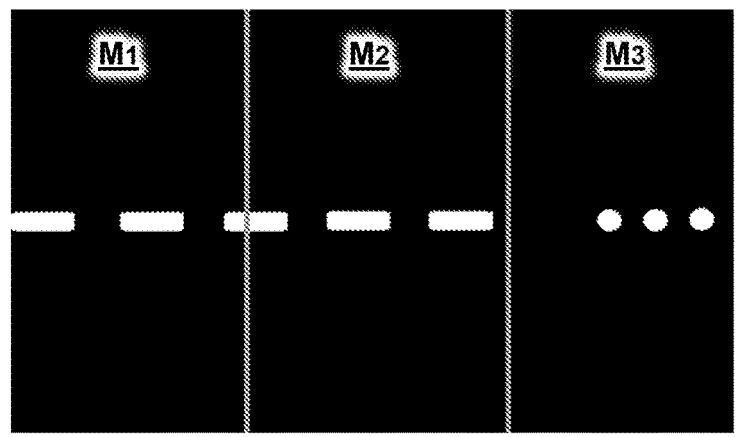
FIGS. 6A-6C illustrate different mask patters of products moving with different friction according to an embodiment.
Figure 6B:
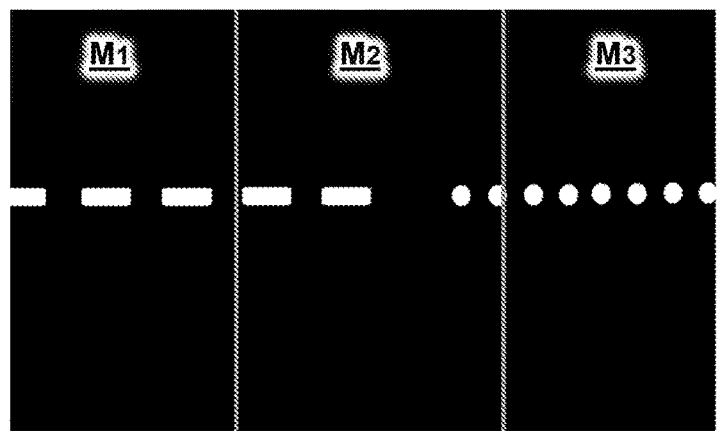
Figure 6C:
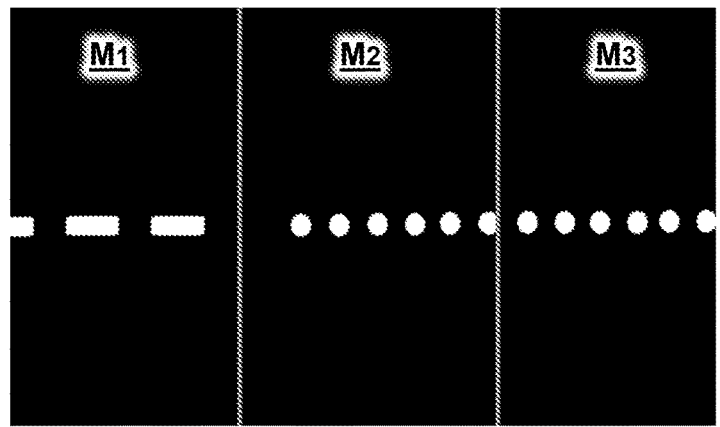

FIGS. 6A-6C illustrate different mask patters of products moving with different friction according to an embodiment. In one embodiment, e.g. as shown, images are captured with a relatively low frame rate or high shutter time relative to a velocity of the products. This may cause the products to appear more or less 'smeared out' depending on their velocity. For example a longer smear may correspond to a higher velocity and a shorter smear to a lower velocity. It will be appreciated that the velocity of products at a specific point or region in the measurement zone M can be used to deduce the level of preceding acceleration or deceleration. In one embodiment, a length of the smear is used to directly determine a velocity of the corresponding product. In another or further embodiment, the total number of pixels per product representation (e.g. interconnected pixels) is used to determine the velocity and/or (previous) acceleration of products. In some embodiments, the measurement zone M is divided in different regions M1, M2, M3. In another or further embodiment, one or more of a position, velocity, and/or acceleration of products is compared between different measurement zones, e.g. by counting the number of pixels in each zone. In one embodiment, the total number of pixels per region is used to determine a velocity of the products. In some embodiments, a threshold can be set for a predetermined acceleration, e.g. based on the number of pixels or otherwise.

FIG. 6A illustrates a scenario wherein products (moving from left to right) are not sufficient decelerated, i.e. the friction is too low. This can be determined e.g. from the number of pixels in a measurement region exceeding a threshold. Optionally the number of pixels in one region is compared with the number of pixels in other regions to determine the threshold. FIG. 6B illustrates another scenario wherein the products are decelerated at a desired friction coefficient. In this case, the smears of high velocity products only partially cross the region M2. FIG. 6C illustrates yet another scenario wherein the products are decelerated too much, i.e. the friction is too high. In this case, there are no smears of high velocity products in the region M2. Depending on whether the friction being to high or too low, a control signal can be generated to start or stop lubrication and/or cleaning of the conveyor surface.

Figure 7A:
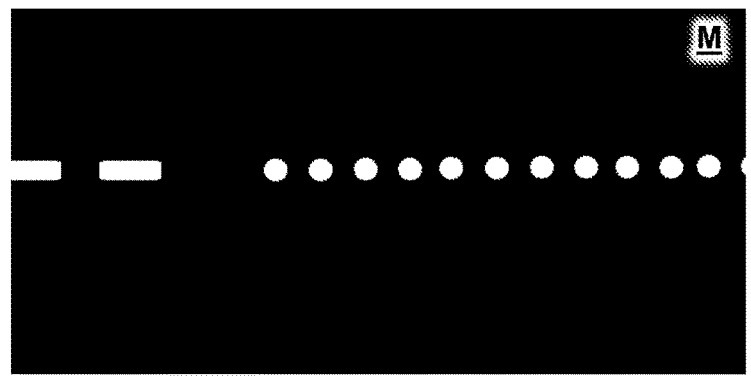
FIGS. 7A-7C illustrate different mask patters of products moving with different friction according to an embodiment
Figure 7B:
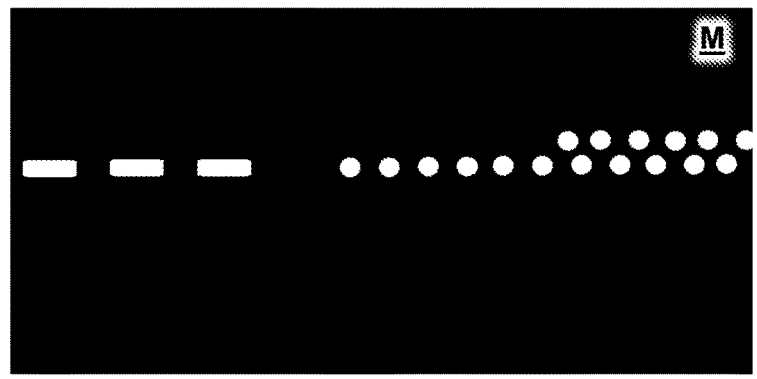
Figure 7C:
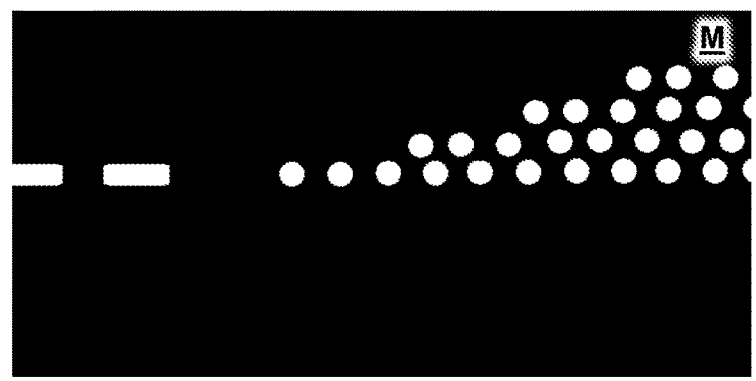

FIGS. 7A-7C illustrate another embodiment with different mask patters of products moving with different friction coefficients. For example, the total number of pixels within the measurement zone is determined to calculate a control signal for controlling a friction adjustment device. For example: when the pixel count is between upper and lower threshold values, the friction is acceptable; when the pixel count exceeds the upper threshold value, friction is too high; when the pixel count is below the lower threshold value, friction is too low. Of course these are only examples which may be reversed depending whether products are accelerating or decelerating in the measurement zone M.

Figure 8A:
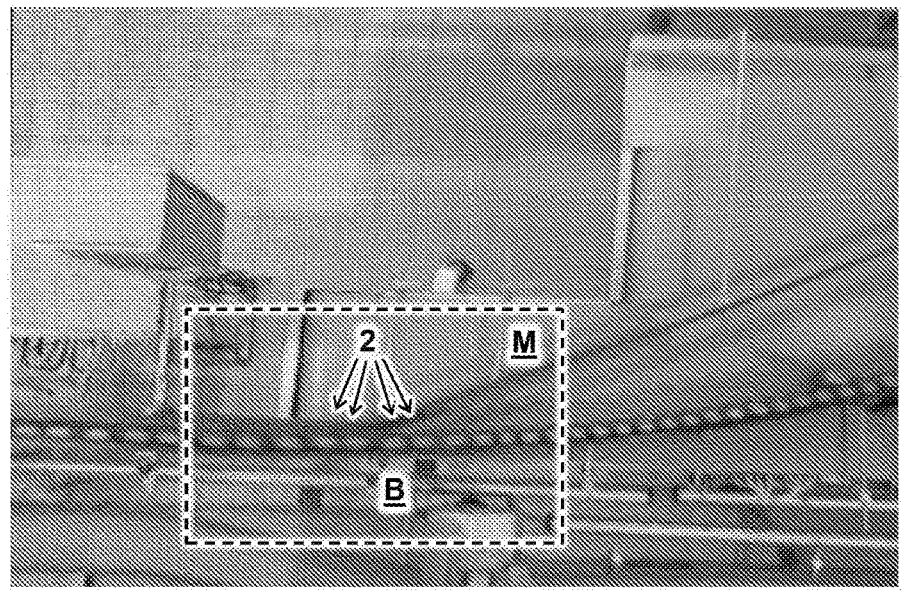
FIGS. 8A and 8B are similar to FIGS. 5A and 5B, but with a relatively dense collection of products
Figure 8B:
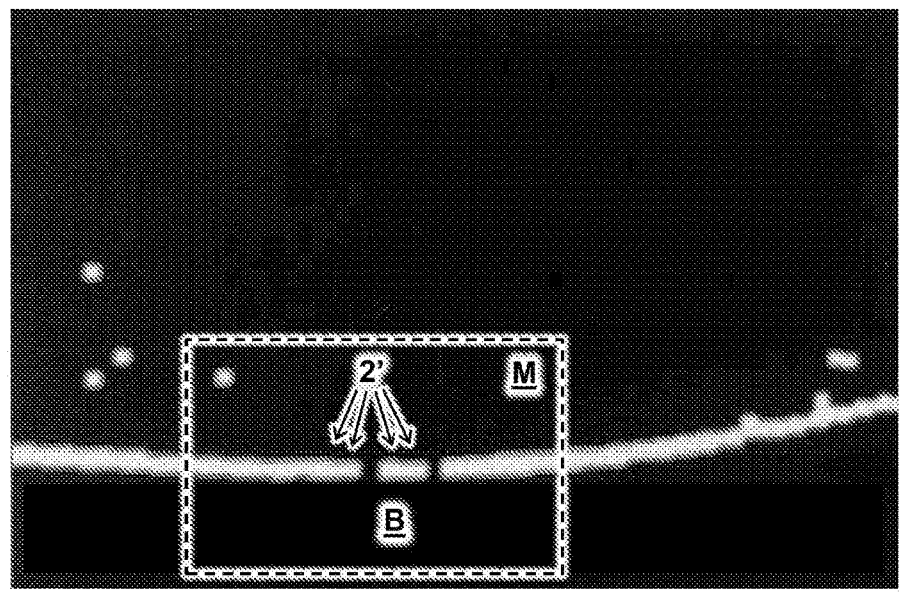

FIGS. 8A and 8B are similar to FIGS. 5A and 5B, but with a relatively dense collection of products 2. In this case the density is so high that the mask image of the products 2' almost forms a continuous stream. This can make it difficult to determine individual positions and/or velocities. Still the acceleration can be deduced from a suitable threshold, e.g. based on a position where the break "B" occurs between high velocity products on the left and low velocity products on the right. It will thus be appreciated that friction and/or acceleration may be deduced from a characteristic of the mask pattern acting like a "barcode".

Figure 9A:
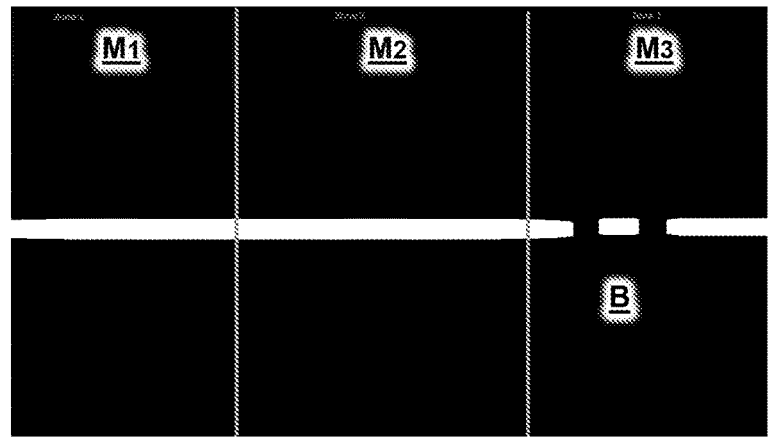
FIGS. 9A-9C illustrate different mask patters of products moving with different friction according to an embodiment
Figure 9B:
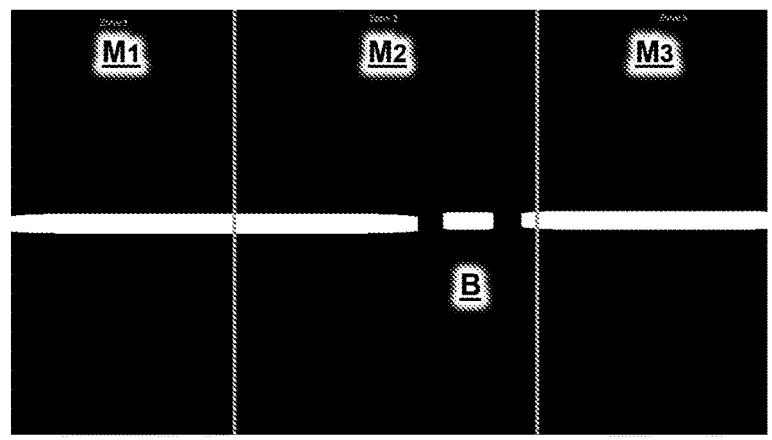
Figure 9C:
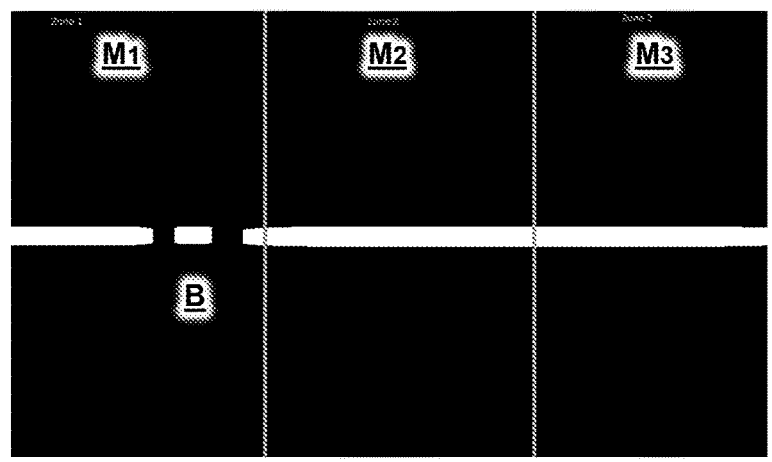

FIGS. 9A-9C illustrate mask patters similar to the example of FIG. 8B but with products moving at different friction coefficients. In the scenario of FIG. 9A, friction is too low causing the break "B" between high and low velocity products occurring only at the last region M3. In the scenario of FIG. 9B, friction is acceptable when the break "B" between high and low velocity products occurring only at the desired region M2. In the scenario of FIG. 9C, friction is too high causing the break "B" between high and low velocity products occurring already at the first region M1. Control of the lubrication and/or cleaning can be set accordingly to keep the break "B" in the intermediate region M2.

Figure 10:
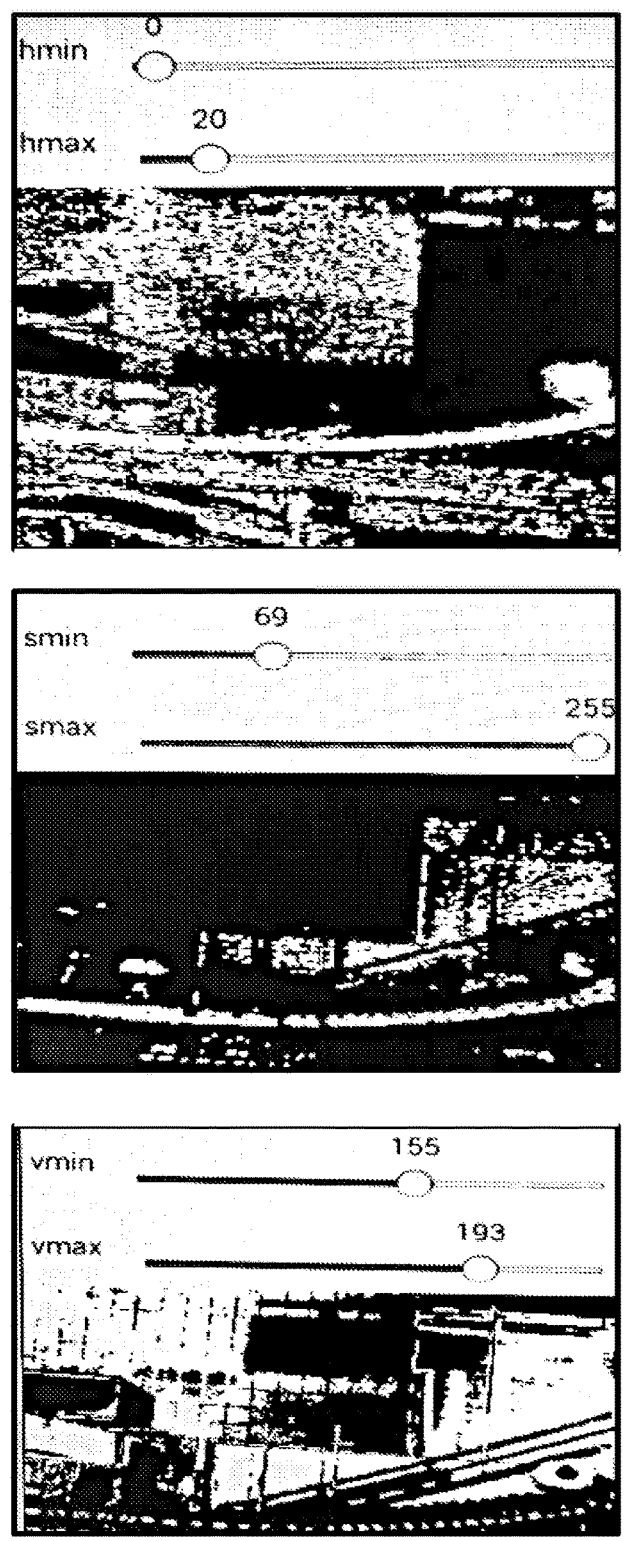
FIG. 10 illustrates an interface for adjusting a mask pattern using HSV controls.

FIG. 10 illustrates an example graphical user interface for adjusting a mask pattern based on HSV controls. The top image shows mask selection based on a hue (H) of the pixels. The middle image shows mask selection based on a saturation (S) of the pixels. The middle image shows mask selection based on a value (V) of the pixels, also referred to as brightness. A final mask may comprise e.g. a combined (AND) operation of the selected thresholds. Of course also other types of masks may be used that can be based on pixel color or otherwise, e.g. inter-frame or intra-frame. The images to be masked can be based on visible, e.g. colour images, infrared images, UV images, or otherwise. Also combinations are possible, e.g. masking at one or more wavelengths.

Figure 11A:
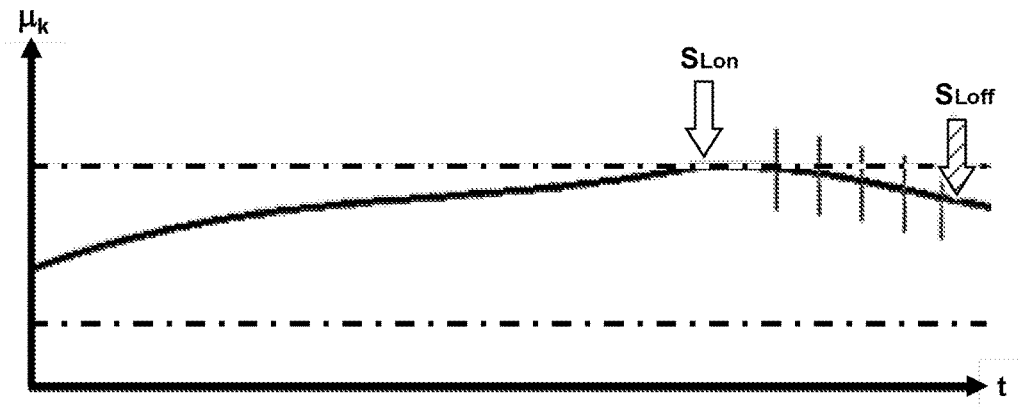
FIGS. 11A-11C illustrate graphs of friction as a function of time for different scenarios.
Figure 11B:
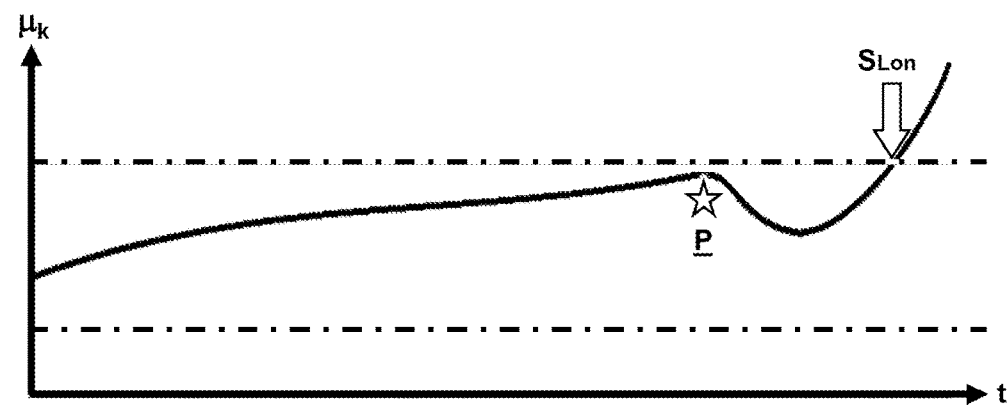
Figure 11C:
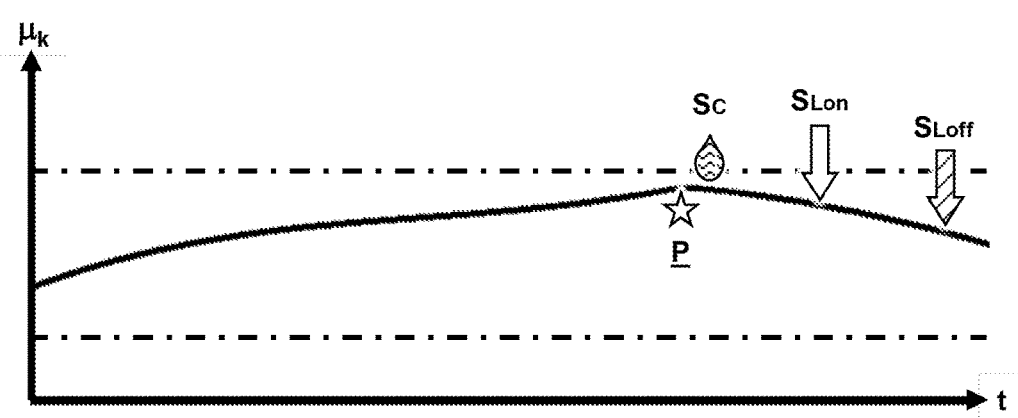

FIGS. 11A-11C illustrate graphs of friction "μk" as a function of time "t" for different scenarios. In a preferred embodiment, the friction or a parameter equivalent thereto is directly or indirectly determined based on measurements indicative of an acceleration or deceleration of products on a conveyor surface as described herein.

FIG. 11A illustrates a scenario wherein the friction gradually increases over time (which is expected) until an upper threshold for the friction is exceeded as indicated by the dash-dotted line. Upon exceeding the threshold, a control signal $S_{Lon}$ is executed which may initiate a lubrication cycle. This may result in decreasing the friction coefficient. For example, the friction coefficient may be sampled at regular intervals indicated by the vertical lines and upon reaching an acceptable friction, the lubrication cycle may be ended by a control signal $S_{Loff}$. The friction may still continue to decrease in some cases e.g. due to a time lag between application of lubrication fluid and result effects on the friction.

FIG. 11B illustrates a scenario wherein at some point in time spillage "P" occurs. For example, a product, e.g. bottle, may spill its contents over the conveyor surface. As indicated in the graph, the spillage "P" may initially have a lubricating effect while the contents are still wet. However, at some later point in time, the contents may dry up leaving e.g. a sugary residue. This may result in an increased friction that may even persist despite initiating a lubrication cycle with the control signal $S_{Lon}$. Such a scenario is typically undesired.

FIG. 11C illustrates a similar scenario as FIG. 11B, but in this case a cleaning cycle is initiated by control signal Sc upon detection of the spillage "P". Preferably this results in timely cleaning of the conveyor surface before the sticky contents of the product dry up. After cleaning the conveyor, optionally, a lubrication cycle is initiated to replenish the lubricant which may have been cleaned off together with the spillage. In one embodiment, cleaning of the conveyor surface is automatically performed based on detection of spillage. In a further embodiment, the spillage is inferred from a (sudden unexpected) decrease of the friction coefficient to trigger a cleaning cycle.

For the purpose of clarity and a concise description, features are described herein as part of the same or separate embodiments, however, it will be appreciated that the scope of the invention may include embodiments having combinations of all or some of the features described. For example, while embodiments were shown for the use of an optically measured acceleration of products on a conveyor surface for controlling a kinetic friction coefficient between the conveyor surface and the products, also alternative ways may be envisaged by those skilled in the art having the benefit of the present disclosure for achieving a similar function and result. E.g. electrical and optical devices may be combined or split up into one or more alternative components. The various elements of the embodiments as discussed and shown offer certain advantages, such as controlling product transport. Of course, it is to be appreciated that any one of the above embodiments or processes may be combined with one or more other embodiments or processes to provide even further improvements in finding and matching designs and advantages. It is appreciated that this disclosure offers particular advantages to transport of bottles and cans between conveyor belts, and in general can be applied for any application wherein control over acceleration or deceleration of products on a surface is desired.

Finally, the above-discussion is intended to be merely illustrative of the present systems and/or methods and should not be construed as limiting the appended claims to any particular embodiment or group of embodiments. The specification and drawings are accordingly to be regarded in an illustrative manner and are not intended to limit the scope of the appended claims. In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage. In particular, all working combinations of the claims are considered inherently disclosed.

The invention claimed is:

1. A method of transporting products, the method comprising
   providing a conveyor surface moving at a conveyor velocity;
   providing products on the conveyor surface in a measurement zone, wherein the products move through the measurement zone with a product velocity that is at least initially different than the conveyor velocity, wherein a contact between the products and the conveyor surface, having different velocity than the products, causes the products to accelerate or decelerate in the measurement zone depending on a kinetic friction coefficient there between;
   receiving a control signal indicative of the acceleration or deceleration of the products in the measurement zone; and
   controlling the kinetic friction coefficient based on the control signal to keep the acceleration or deceleration within a predetermined threshold range.

2. The method according to claim 1, wherein the control signal is based on a sensor signal indicative of a time-dependent position of one or more of the products in the measurement zone.

3. The method according to claim 1, wherein the control signal is based on an optical measurement of an acceleration or deceleration of one or more of the products in the measurement zone.

4. The method according to claim 1, comprising recording a sequence of images of the measurement zone where the products are accelerating or decelerating as a result of contacting the conveyor surface; wherein a time-dependent position of at least one of the products is determined based on the recorded images; wherein the control signal is based on the time-dependent position of the at least one of the products.

5. The method according to claim 1, wherein the kinetic friction coefficient is controlled by changing a surface property of the conveyor surface and/or surface of the products.

6. The method according to claim 1, wherein the kinetic friction coefficient is controlled by applying a controlled amount of lubricant to the conveyor surface and/or the products.

7. The method according to claim 1, wherein the kinetic friction coefficient is controlled by controlling a degree of cleaning of the conveyor surface.

8. The method according to claim 1, wherein the products are bottles, wherein the threshold range is set to prevent toppling of the bottles as a result of excessive acceleration or deceleration.

9. A system for transporting products, the system comprising
   a conveyor surface configured to move at a conveyor velocity, wherein the products are guided onto the conveyor surface to move through the measurement zone with a product velocity that is at least initially different than the conveyor velocity, wherein a contact between the products and the conveyor surface, having different velocity than the products, causes the products to accelerate or decelerate in the measurement zone depending on a kinetic friction coefficient there between;
   a sensor configured to measure the acceleration or deceleration of the products in the measurement zone for calculating a control signal indicative of the acceleration or deceleration; and
   a friction adjustment device configured to receive the control signal and control the kinetic friction coefficient based on the control signal to keep the acceleration or deceleration within a predetermined threshold range.

10. The system according to claim 9, wherein the sensor comprises an optical sensor configured to optically measure a time-dependent position of the products.

11. The system according to claim 10, wherein the optical sensor is a camera configure to record images, the system comprising an image processor configured to process recorded images and calculate a time-dependent position of one or more of the products based on the recorded images, wherein the image processor is programmed with image recognition software to recognize a visual marker associated with part of a product and track a position of the visual marker between different images.

12. The system according to claim 9, wherein the conveyor surface is a destination conveyor surface, the system further comprising an origin conveyor surface configured to lead the products from the origin conveyor surface to the destination conveyor surface, wherein a transition from the origin conveyor surface to the destination conveyor surface causes the products to accelerate or decelerate in the measurement zone on the destination conveyor surface.

13. The system according to claim 9, comprising a holding device configured to temporarily hold a position of one or more of the products while they are on the conveyor surface, wherein the measurement zone is behind the holding device to measure acceleration of one or more of the products after being released from the holding device.

14. Use of an optical measurement of products on a conveyor surface for automatically controlling a kinetic friction coefficient between the conveyor surface and the products, wherein the products are guided onto the conveyor surface to move through a measurement zone for the optical measurement with a product velocity that is at least initially different than the conveyor velocity, wherein a contact between the products and the conveyor surface, having different velocity than the products, causes the products to accelerate or decelerate in the measurement zone depending on the kinetic friction coefficient there between.

* * * * *